US008859701B2

(12) United States Patent
Loick et al.

(10) Patent No.: US 8,859,701 B2
(45) Date of Patent: Oct. 14, 2014

(54) PROCESS FOR PRODUCING IMPROVED ABSORBENT POLYMERS BY MEANS OF CRYOGENIC GRINDING

(75) Inventors: Christoph Loick, Tonisvorst (DE); Dominik Gartz, Viersen (DE); Laurent Wattebled, Dusseldorf (DE); Jorg Harren, Baesweiler (DE)

(73) Assignee: Evonik Degussa GmbH, Essen (DE)

( * ) Notice: Subject to any disclaimer, the term of this patent is extended or adjusted under 35 U.S.C. 154(b) by 32 days.

(21) Appl. No.: 13/876,736

(22) PCT Filed: Oct. 5, 2011

(86) PCT No.: PCT/EP2011/067348
§ 371 (c)(1),
(2), (4) Date: Jun. 11, 2013

(87) PCT Pub. No.: WO2012/055681
PCT Pub. Date: May 3, 2012

(65) Prior Publication Data
US 2014/0045683 A1  Feb. 13, 2014

(30) Foreign Application Priority Data
Oct. 29, 2010  (DE) .................. 10 2010 043 113

(51) Int. Cl.
*C08J 9/36* (2006.01)
*C08F 20/06* (2006.01)
*C08J 3/12* (2006.01)
*A61L 15/60* (2006.01)
*A61L 15/22* (2006.01)
*C08F 6/00* (2006.01)
*C08J 3/24* (2006.01)
*B01J 20/26* (2006.01)

(52) U.S. Cl.
CPC ............ *B01J 20/267* (2013.01); *C08J 2300/14* (2013.01); *C08J 3/12* (2013.01); *A61L 15/60* (2013.01); *A61L 15/22* (2013.01); *C08F 6/008* (2013.01); *C08J 3/245* (2013.01); *C08J 2333/00* (2013.01)
USPC ........... 526/317.1; 521/64; 264/140; 502/402

(58) Field of Classification Search
USPC ..................................... 526/317.1
See application file for complete search history.

(56) References Cited

U.S. PATENT DOCUMENTS

| 4,076,663 | A | 2/1978 | Masuda et al. |
| 4,179,367 | A | 12/1979 | Barthell et al. |
| 4,286,082 | A | 8/1981 | Tsubakimoto et al. |
| 4,587,308 | A | 5/1986 | Makita et al. |
| 5,149,335 | A | 9/1992 | Kellenberger et al. |
| 5,409,771 | A | 4/1995 | Dahmen et al. |
| 5,610,220 | A | 3/1997 | Klimmek et al. |
| 5,672,633 | A | 9/1997 | Brehm et al. |
| 5,712,316 | A | 1/1998 | Dahmen et al. |
| 6,087,450 | A | 7/2000 | Breitbach et al. |
| 6,100,305 | A * | 8/2000 | Miyake et al. ................. 521/53 |
| 6,143,821 | A | 11/2000 | Houben |
| 6,333,109 | B1 * | 12/2001 | Harada et al. ................. 428/402 |
| 6,605,673 | B1 | 8/2003 | Mertens et al. |
| 6,620,889 | B1 | 9/2003 | Mertens et al. |
| 6,623,576 | B2 * | 9/2003 | Mitchell et al. .............. 156/62.2 |
| 6,623,848 | B2 | 9/2003 | Brehm et al. |
| 6,831,142 | B2 | 12/2004 | Mertens et al. |
| 7,179,862 | B2 | 2/2007 | Mertens et al. |
| 7,285,599 | B2 | 10/2007 | Mertens et al. |
| 7,572,864 | B2 | 8/2009 | Mertens et al. |
| 7,625,957 | B2 | 12/2009 | Harren et al. |
| 7,683,150 | B2 * | 3/2010 | Higashimoto et al. ...... 526/317.1 |
| 7,728,079 | B2 | 6/2010 | Harren et al. |
| 7,833,624 | B2 | 11/2010 | Harren et al. |
| 8,048,942 | B2 | 11/2011 | Fricker et al. |
| 8,063,121 | B2 | 11/2011 | Fricker et al. |
| 8,198,385 | B2 | 6/2012 | Gartner et al. |
| 8,252,873 | B1 | 8/2012 | Gartner et al. |

(Continued)

FOREIGN PATENT DOCUMENTS

| DE | 2612846 |  | 10/1976 |
| DE | 2706135 | A1 | 8/1978 |
| DE | 3503458 | A1 | 8/1985 |
| DE | 4020780 | C1 | 8/1991 |
| DE | 4244548 | A1 | 7/1994 |
| DE | 4418818 | A1 | 1/1995 |
| DE | 4333056 | A1 | 3/1995 |
| DE | 19543366 | A1 | 5/1997 |
| DE | 19543368 | A1 | 5/1997 |
| EP | 0443627 | A2 | 8/1991 |
| EP | 0876888 | A1 | 11/1998 |
| WO | 9934843 | A1 | 7/1999 |
| WO | 02056812 | A2 | 7/2002 |

OTHER PUBLICATIONS

Naumann et al., U.S. Appl. No. 13/341,132, filed Dec. 30, 2011.
Naumann et al., U.S. Appl. No. 13/780,672, filed Feb. 28, 2013.

*Primary Examiner* — Vu A Nguyen
(74) *Attorney, Agent, or Firm* — Smith Moore Leatherwood LLP; Philip P. McCann; John P. Zimmer

(57) ABSTRACT

A process for producing a water-absorbing polymer comprises: (i) mixing ($\alpha$1) 0.1-99.99% by weight of ethylenically unsaturated monomers containing acid groups or salts thereof, or ethylenically unsaturated monomers including a protonated or quaternized nitrogen, or mixtures thereof, ($\alpha$2) 0-70% by weight of ethylenically unsaturated monomers copolymerizable with ($\alpha$1), ($\alpha$3) 0.001-10% by weight of one or more crosslinkers, ($\alpha$4) 0-30% by weight of water-soluble polymers, and ($\alpha$5) 0-20% by weight of one or more assistants, where the sum of the weights ($\alpha$1) to ($\alpha$5) is 100%; (ii) free-radical polymerization with crosslinking to form an untreated hydrogel polymer; (iii) coarse comminution of the untreated hydrogel polymer to give pieces having a diameter from 0.1 mm to 5.0 cm; (iv) cooling and grinding the untreated hydrogel polymer; (v) drying the untreated hydrogel polymer after grinding at a temperature from 85° C. to 260° C.; (vi) postcrosslinking the hydrogel polymer and (vii) drying the water-absorbing polymer.

12 Claims, No Drawings

(56) References Cited

U.S. PATENT DOCUMENTS

| | | |
|---|---|---|
| 8,349,913 B2 | 1/2013 | Harren et al. |
| 8,357,766 B2 | 1/2013 | Fricker et al. |
| 2007/0065503 A1 | 3/2007 | Harren et al. |
| 2007/0129495 A1 | 6/2007 | Mertens et al. |
| 2010/0036004 A1 | 2/2010 | Harren et al. |
| 2010/0105808 A1 | 4/2010 | Fricker et al. |
| 2010/0130950 A1 | 5/2010 | Harren et al. |
| 2010/0209379 A1 | 8/2010 | Furno et al. |
| 2011/0009272 A1 | 1/2011 | Wattebled et al. |
| 2012/0001122 A1 | 1/2012 | Wattebled et al. |
| 2012/0145956 A1 | 6/2012 | Walden et al. |
| 2012/0302445 A1 | 11/2012 | Rudolph et al. |
| 2012/0309905 A1 | 12/2012 | Fricker et al. |

\* cited by examiner

US 8,859,701 B2

PROCESS FOR PRODUCING IMPROVED ABSORBENT POLYMERS BY MEANS OF CRYOGENIC GRINDING

This application is a national stage application under 35 U.S.C. §371 of International Application No. PCT/EP2011/067348 filed 5 Oct. 2011, which claims priority to German Application No. DE 10 2010 043 113.3 filed 29 Oct. 2010, the disclosures of which are expressly incorporated herein by reference.

FIELD

The present invention relates to a process for producing improved absorbent polymers by means of cryogenic grinding before drying, to use of an absorbent polymer, to a process for producing a composite and to use of a composite.

BACKGROUND

Superabsorbents are water-insoluble crosslinked polymers which are capable of swelling and forming hydrogels to absorb large amounts of aqueous liquids, especially body fluids, preferably urine or blood, and of retaining them under a particular pressure. By virtue of these characteristic properties, these polymers are employed principally in incorporation into sanitary articles, for example nappies, incontinence products or sanitary towels.

Superabsorbents are generally produced by the free-radical polymerization of monomers bearing acid groups in the presence of crosslinkers. Through the selection of the monomer composition, of the crosslinkers and of the polymerization conditions and the processing properties for the hydrogel obtained after the polymerization, it is possible to produce polymers with different absorber properties. Further possibilities are offered by the production of graft polymers, for example using chemically modified starch, cellulose and polyvinyl alcohol according to DE-A 26 12 846.

EP 876 888 A1 discloses a process in which the hydrogel is frozen and comminuted by means of a system consisting of rotating blades, and then dried and ground. The advantage is said to be that the pore structure is preserved since it is frozen before the first coarse comminution. A disadvantage here is that it is in principle necessary here to use a foaming agent in order to obtain the surface pore structure. In addition, a higher proportion of ultrafine particles is obtained in this comminution of the frozen hydrogel. Likewise, a higher energy expenditure and also a more complex technical solution are required for the comminution of the cooled hydrogel.

For formation of what are called "absorbent" polymers, polymerization of different kinds of normally water-soluble monomers is required, often also together with water-insoluble comonomers in the presence of crosslinkers. The crosslinkers are added during or after the polymerization. Such absorbent polymers are lightly crosslinked, water-insoluble hydrogel polymers which, in the dry and essentially anhydrous state, have a great ability to absorb water. This can amount to several times their own weight. Due to the high absorption capacity, the absorbent polymers are suitable for incorporation into water-absorbing structures and articles, for example nappies, incontinence products or sanitary towels. These absorbent polymers are also referred to in the literature as "superabsorents". In this context, reference is made to Modern Superabsorbent Polymer Technology; F. L. Buchholz, A. T. Graham, Wiley-VCH, 1998.

The demand for thinner hygiene articles has increased markedly in the last few years. Predominantly thinner nappies which contain less fluff pulp are now being produced. The task of the fluff pulp accordingly has to be assumed by the absorbent polymer without any resulting loss of quality. Such polymers are produced in the presence of solvents, preferably water.

In order to optimize the properties, especially the absorption properties, of the superabsorbents for use in hygiene articles, the polymer particles, polymer gel obtained after drying and after comminution, are modified, preferably surface modified. The surface modification can give rise to a core-shell-like morphology, which is preferred especially in the case of superabsorbent particles. This modification serves, for example, to provide the superabsorbents with odour-binding properties, to improve the dusting characteristics of the superabsorbents, to reduce the caking of the superabsorbent particles, to improve the absorption capacity of the superabsorbents under pressure stress and/or to advantageously affect the permeability properties of the superabsorbent.

SUMMARY

The present invention includes various embodiments as set forth herein.

In general terms, it is an object of the present invention to provide a water-absorbing polymer which has an improved swelling rate with simultaneous preservation of the overall quality. In addition, a simpler technical solution for the comminution of the hydrogel shall be provided, which does not have the disadvantages of the prior art.

It is a particular object of the present invention to provide a process by which it is possible to produce absorbent polymers, ensuring a particularly high swelling rate which can be achieved as early as before the first drying.

DETAILED DESCRIPTION

The invention provides a process for producing a superabsorbent polymer composition, said process comprising the following steps:
(i) mixing
($\alpha$1) 0.1 to 99.99% by weight, preferably 20 to 98.99% by weight and more preferably 30 to 98.95% by weight of polymerized, ethylenically unsaturated monomers containing acid groups or salts thereof, or polymerized, ethylenically unsaturated monomers including a protonated or quaternized nitrogen, or mixtures thereof, particular preference being given to mixtures including at least ethylenically unsaturated monomers containing acid groups, preferably acrylic acid, optionally in partly neutralized form,
($\alpha$2) 0 to 70% by weight, preferably 1 to 60% by weight and more preferably 1 to 40% by weight of polymerized, ethylenically unsaturated monomers copolymerizable with ($\alpha$1),
($\alpha$3) 0.001 to 10% by weight, preferably 0.01 to 7% by weight and more preferably 0.05 to 5% by weight of one or more crosslinkers,
($\alpha$4) 0 to 30% by weight, preferably 1 to 20% by weight and more preferably 5 to 10% by weight of water-soluble polymers, and
($\alpha$5) 0 to 20% by weight, preferably 0.01 to 7% by weight and more preferably 0.05 to 5% by weight of one or more assistants, where the sum of the weights ($\alpha$1) to ($\alpha$5) is 100% by weight;
(ii) free-radical polymerization with crosslinking to form a water-insoluble aqueous untreated hydrogel polymer;

(iii) coarse comminution of the untreated hydrogel polymer to give pieces having a diameter in the range from 0.1 mm to 5.0 cm;
(iv) cooling the precomminuted untreated hydrogel polymer and grinding the cooled untreated hydrogen polymer;
(v) drying the comminuted untreated hydrogel polymer after grinding at a temperature in the range from 85° C. to 260° C., and sieving the dried pieces in the range from 155 μm to 850 μm;
(vi) postcrosslinking the hydrogel polymer and
(vii) drying and finishing the water-absorbing polymer.

In a further embodiment, the product produced by the process according to the invention is mixed with standard superabsorbents in step (ii) and/or (iii) and then produced according to the further steps.

In a further embodiment, standard superabsorbents can be added in steps (v) or (vi) or (vii).

In a further embodiment, the product produced by the process according to the invention is mixed with precursors of other standard superabsorbents in steps (ii) and/or (iii), and processed further according to the further steps.

In the process according to the invention, after step (ii), the hydrogel polymer is comminuted in a first step and then cooled in a cooling region to −30° C. to −200° C. and comminuted further.

Preference is given to the addition of the standard superabsorbent after steps (v) to (vii). Preference is likewise given to the addition of the standard superabsorbent after step (i).

Advantageously, in this step, the particle size can be adjusted before the drying of the gel, in contrast to the prior art to date where this is not possible.

According to the invention, the comminuted untreated hydrogel polymer is cooled in the cooling region over a period of 30 sec to 3600 sec before it is processed further. The coolants used are inert solid or liquid refrigerants from the group of CO, carbon dioxide, inert hydrocarbons such as short-chain aliphatics (methane, ethane, propane), halogenated hydrocarbons, nitrogen, helium, argon, or other inert gases which liquefy at temperatures below −30° C., or mixtures thereof. Preference is given to solid carbon dioxide, and to liquid helium and nitrogen.

In the process according to the invention, the cooling region has at least one cooling zone. The cooling region has a temperature gradient, it being possible to set the lower temperatures at the start or at the end of the cooling region.

In a further embodiment, the cooling region consists of at least two cooling zones. In one embodiment, these may have a temperature gradient over the two cooling zones, or else the first or last cooling zone has the temperature gradient and at least one other has a defined temperature.

According to the invention, the cooling zones in one variant may be of equal length. In a further embodiment, the cooling zone with the temperature gradient is shorter than the cooling zone without temperature gradient. The cooling zones can be provided with different inert coolants.

In addition, the cooling region has, in the end region, a cooled apparatus for grinding of the comminuted untreated hydrogel polymer. This apparatus may be a grinder, kneader, extruder, crusher, blade or roller. Preference is given to mills, kneaders or extruders.

Advantageously, both the water-absorbing polymer and the comminuted untreated hydrogel polymer have an FSR of at least 0.3, preferably 0.4 and more preferably of 0.6.

The monoethylenically unsaturated monomers ($\alpha 1$) containing acid groups may be partly or fully, preferably partly, neutralized. The monoethylenically unsaturated monomers containing acid groups are preferably neutralized to an extent of at least 10 mol %, more preferably to an extent of at least 25 to 50 mol % and further preferably to an extent of 50 to 90 mol %. The monomers ($\alpha 1$) can be neutralized either before or after the polymerization. In this case, the partial neutralization is effected to an extent of at least 10 mol %, more preferably to an extent of 25 to 50 mol % and further preferably to an extent of 50 to 90 mol %. In addition, neutralization can be effected with alkali metal hydroxides, alkaline earth metal hydroxides, ammonia, and carbonates and bicarbonates. In addition, any further base which forms a water-soluble salt with the acid is conceivable. Mixed neutralization with different bases is also conceivable. Preference is given to neutralization with ammonia or with alkali metal hydroxides, more preferably with sodium hydroxide or with ammonia.

In addition, the free acid groups in a polymer may predominate, such that this polymer has a pH within the acidic range. This acidic water-absorbing polymer may be at least partly neutralized by a polymer with free basic groups, preferably amine groups, which is basic compared to the acid polymer. These polymers are referred to in the literature as "*Mixed-Bed Ion-Exchange Absorbent Polymers*" (MBIEA polymers) and are disclosed inter alia in WO 99/34843. The disclosure of WO 99/34843 is hereby incorporated by reference and is therefore considered to form part of the disclosure. In general, MBIEA polymers constitute a composition which includes firstly basic polymers capable of exchanging anions, and secondly a polymer which is acidic compared to the basic polymer and is capable of exchanging cations. The basic polymer has basic groups and is typically obtained by the polymerization of monomers which bear basic groups or groups which can be converted to basic groups. These monomers are in particular those which have primary, secondary or tertiary amines or the corresponding phosphines, or at least two of the above functional groups. This group of monomers includes especially ethyleneamine, allylamine, diallylamine, 4-aminobutene, alkyloxycyclines, vinylformamide, 5-aminopentene, carbodiimide, formaldacine, melamine and the like, and the secondary or tertiary amine derivatives thereof.

Preferred monoethylenically unsaturated monomers ($\alpha 1$) containing acid groups are acrylic acid, methacrylic acid, ethacrylic acid, $\alpha$-chloroacrylic acid, $\alpha$-cyanoacrylic acid, $\beta$-methylacrylic acid (crotonic acid), $\alpha$-phenylacrylic acid, $\beta$-acryloyloxypropionoic acid, sorbic acid, $\alpha$-chlorosorbic acid, 2'-methylisocrotonic acid, cinnamic acid, p-chlorocinnamic acid, $\beta$-stearyl acid, itaconic acid, citraconic acid, mesaconic acid, glutaconic acid, aconitic acid, maleic acid, fumaric acid, tricarboxyethylene and maleic anhydride, preference being given particularly to acrylic acid and methacrylic acid and additionally to acrylic acid.

In addition to these monomers containing carboxylate groups, preferred monoethylenically unsaturated monomers ($\alpha 1$) containing acid groups additionally include ethylenically unsaturated sulphonic acid monomers or ethylenically unsaturated phosphonic acid monomers.

Preferred ethylenically unsaturated sulphonic acid monomers are allylsulphonic acid or aliphatic or aromatic vinylsulphonic acids or acrylic or methacrylic sulphonic acids. Preferred aliphatic or aromatic vinylsulphonic acids are vinylsulphonic acid, 4-vinylbenzylsulphonic acid, vinyltoluenesulphonic acid and styrenesulphonic acid. Preferred acryloyl- or methacryloylsulphonic acids are sulphoethyl(meth)acrylate, sulphopropyl(meth)acrylate, 2-hydroxy-3-methacryloyloxypropylsulphonic acid, and (meth)acrylamidoalkylsulphonic acids such as 2-acrylamido-2-methylpropanesulphonic acid.

Preferred ethylenically unsaturated phosphonic acid monomers are vinylphosphonic acid, allylphosphonic acid, vinylbenzylphosphonic acid, (meth)acrylamidoalkylphosphonic acids, acrylamidoalkyldiphosphonic acids, phosphonomethylated vinylamines and (meth)acryloylphosphonic acid derivatives.

Preferred ethylenically unsaturated monomers (α1) containing a protonated nitrogen are preferably dialkylaminoalkyl(meth)acrylates in protonated form, for example dimethylaminoethyl(meth)acrylate hydrochloride or dimethylaminoethyl(meth)acrylate hydrosulphate, and dialkylaminoalkyl(meth)acrylamides in protonated form, for example dimethylaminoethyl(meth)acrylamide hydrochloride, dimethylaminopropyl(meth)acrylamide hydrochloride, dimethylaminopropyl(meth)acrylamide hydrosulphate or dimethylaminoethyl-(meth)acrylamide hydrosulphate.

Preferred ethylenically unsaturated monomers (α1) containing a quaternized nitrogen are dialkylammonioalkyl (meth)acrylates in quaternized form, for example trimethylammonioethyl(meth)acrylate methosulphate or dimethylethylammonioethyl(meth)acrylate ethosulphate, and (meth)acrylamidoalkyldialkylamines in quaternized form, for example (meth)acrylamidopropyltrimethylammonium chloride, trimethylammonioethyl(meth)acrylate chloride or (meth)acrylamidopropyltrimethylammonium sulphate.

Preferred monoethylenically unsaturated monomers (α2) copolymerizable with (α1) are acrylamides and methacrylamides.

Preferred (meth)acrylamides are, in addition to acrylamide and methacrylamide, alkyl-substituted (meth)acrylamides or aminoalkyl-substituted derivatives of (meth)acrylamide, such as N-methylol(meth)acryl amide, N,N-dimethylamino (meth)acrylamide, dimethyl(meth)acrylamide or diethyl (meth)acrylamide. Possible vinylamides are, for example, N-vinylamides, N-vinylformamide, N-vinylacetamide, N-vinyl-N-methylacetamide, N-vinyl-N-methylformamide, vinylpyrrolidone. Among these monomers, particular preference is given to acrylamide.

Additionally preferred as monoethylenically unsaturated monomers (α2) copolymerizable with (α1) are water-dispersible monomers. Preferred water-dispersible monomers are acrylic esters and methacrylic esters, such as methyl (meth)acrylate, ethyl(meth)acrylate, propyl(meth)acrylate or butyl(meth)acrylate, and also vinyl acetate, styrene and isobutylene.

Crosslinkers (α3) preferred in accordance with the invention are compounds having at least two ethylenically unsaturated groups within one molecule (crosslinker class I), compounds having at least two functional groups which can react with functional groups of monomers (α1) or (α2) in a condensation reaction (=condensation crosslinkers), in an addition reaction or in a ring-opening reaction (crosslinker class II), compounds which have at least one ethylenically unsaturated group and at least one functional group which can react with functional groups of monomers (α1) or (α2) in a condensation reaction, in an addition reaction or in a ring-opening reaction (crosslinker class III), or polyvalent metal cations (crosslinker class IV). The compounds of crosslinker class I achieve crosslinking of the polymers through the free-radical polymerization of the ethylenically unsaturated groups of the crosslinker molecule with the monoethylenically unsaturated monomers (α1) or (α2), while the compounds of the crosslinker class II and the polyvalent metal cations of crosslinker class IV achieve crosslinking of the polymers by a condensation reaction of the functional groups (crosslinker class II) or by electrostatic interaction of the polyvalent metal cation (crosslinker class IV) with the functional groups of monomers (α1) or (α2). In the case of the compounds of crosslinker class III, there is correspondingly crosslinking of the polymer both by free-radical polymerization of the ethylenically unsaturated group and by a condensation reaction between the functional group of the crosslinker and the functional groups of monomers (α1) or (α2).

Preferred compounds of crosslinker class I are poly(meth) acrylic esters which are obtained, for example, by the reaction of a polyol, for example ethylene glycol, propylene glycol, trimethylolpropane, 1,6-hexanediol, glycerol, pentaerythritol, polyethylene glycol or polypropylene glycol, of an amino alcohol, of a polyalkylenepolyamine, for example diethylenetriamine or triethylenetetramine, or of an alkoxylated polyol with acrylic acid or methacrylic acid. Preferred compounds of crosslinker class I are additionally polyvinyl compounds, poly(meth)allyl compounds, (meth)acrylic esters of a monovinyl compound or (meth)acrylic esters of a mono (meth)allyl compound, preferably of the mono(meth)allyl compounds of a polyol or of an amino alcohol. In this context, reference is made to DE 195 43 366 and DE 195 43 368. The disclosures are hereby incorporated by reference and therefore form part of the disclosure.

Examples of compounds of crosslinker class I include alkenyl di(meth)acrylates, for example ethylene glycol di(meth) acrylate, 1,3-propylene glycol di(meth)acrylate, 1,4-butylene glycol di(meth)acrylate, 1,3-butylene glycol di(meth)acrylate, 1,6-hexanediol di(meth)acrylate, 1,10-decanediol di(meth)acrylate, 1,12-dodecanediol di(meth)acrylate, 1,18-octadecanediol di(meth)acrylate, cyclopentanediol di(meth) acrylate, neopentyl glycol di(meth)acrylate, methylene di(meth)acrylate or pentaerythritol di(meth)acrylate, alkenyldi(meth)acrylamides, for example N-methyldi(meth) acrylamide, N,N'-3-methylbutylidenebis(meth)acrylamide, N,N'-(1,2-dihydroxyethylene)bis(meth)acrylamide, N,N'-hexamethylenebis(meth)acrylamide or N,N'-methylenebis (meth)acrylamide, polyalkoxy di(meth)acrylates, for example diethylene glycol di(meth)acrylate, triethylene glycol di(meth)acrylate, tetraethylene glycol di(meth)acrylate, dipropylene glycol di(meth)acrylate, tripropylene glycol di(meth)acrylate or tetrapropylene glycol di(meth)acrylate, bisphenol A di(meth)acrylate, ethoxylated bisphenol A di(meth)acrylate, benzylidene di(meth)acrylate, 1,3-di (meth)acryloyloxy-2-propanol, hydroquinone di(meth)acrylate, di(meth)acrylate esters of trimethylolpropane which has preferably been alkoxylated, preferably ethoxylated, with 1 to 30 mol of alkylene oxide per hydroxyl group, thioethylene glycol di(meth)acrylate, thiopropylene glycol di(meth)acrylate, thiopolyethylene glycol di(meth)acrylate, thiopolypropylene glycol di(meth)acrylate, divinyl ethers, for example 1,4-butanediol divinyl ether, divinyl esters, for example divinyl adipate, alkadienes, for example butadiene or 1,6-hexadiene, divinylbenzene, di(meth)allyl compounds, for example di(meth)allyl phthalate or di(meth)allyl succinate, homo- and copolymers of di(meth)allyldimethylammonium chloride and homo- and copolymers of diethyl(meth)allylammoniomethyl(meth)acrylate chloride, vinyl(meth)acryloyl compounds, for example vinyl(meth)acrylate, (meth)allyl (meth)acryloyl compounds, for example (meth)allyl(meth) acrylate, (meth)allyl(meth)acrylate ethoxylated with 1 to 30 mol of ethylene oxide per hydroxyl group, di(meth)allyl esters of polycarboxylic acids, for example di(meth)allyl maleate, di(meth)allyl fumarate, di(meth)allyl succinate or di(meth)allyl terephthalate, compounds having 3 or more ethylenically unsaturated, free-radically polymerizable groups, for example glyceryl tri(meth)acrylate, (meth)acrylate esters of glycerol which has been ethoxylated with preferably 1 to 30 mol of ethylene oxide per hydroxyl group, trimethylolpropane tri(meth)acrylate, tri(meth)acrylate esters of trimethylolpropane which has preferably been alkoxylated, preferably ethoxylated, with 1 to 30 mol of alkylene oxide per hydroxyl group, trimethacrylamide, (meth) allylidene di(meth)acrylate, 3-allyloxy-1,2-propanediol di(meth)acrylate, tri(meth)allyl cyanurate, tri(meth)allyl isocyanurate, pentaerythritol tetra(meth)acrylate, pentaerythritol tri(meth)acrylate, (meth)acrylic esters of pentaerythritol ethoxylated with preferably 1 to 30 mol of ethylene oxide per hydroxyl group, tris(2-hydroxyethyl)isocyanurate tri(meth) acrylate, trivinyl trimellitate, tri(meth)allylamine, di(meth) allylalkylamines, for example di(meth)allylmethylamine, tri (meth)allyl phosphate, tetra(meth)allylethylenediamine, poly(meth)allyl esters, tetra(meth)allyloxyethane or tetra (meth)allylammonium halides.

Preferred compounds of crosslinker class II are compounds which have at least two functional groups which can react in a condensation reaction (=condensation crosslinkers), in an addition reaction or in a ring-opening reaction with the functional groups of monomers ($\alpha 1$) or ($\alpha 2$), preferably with acid groups of monomers ($\alpha 1$). These functional groups of the compounds of crosslinker class II are preferably alcohol, amine, aldehyde, glycidyl, isocyanate, carbonate or epichloro functions.

Examples of compounds of crosslinker class II include polyols, for example ethylene glycol, polyethylene glycols such as diethylene glycol, triethylene glycol and tetraethylene glycol, propylene glycol, polypropylene glycols such as dipropylene glycol, tripropylene glycol or tetrapropylene glycol, 1,3-butanediol, 1,4-butanediol, 1,5-pentanediol, 2,4-pentanediol, 1,6-hexanediol, 2,5-hexanediol, glycerol, polyglycerol, trimethylolpropane, polyoxypropylene, oxyethyleneoxypropylene block copolymers, sorbitan fatty acid esters, polyoxyethylene sorbitan fatty acid esters, pentaerythritol, polyvinyl alcohol and sorbitol, amino alcohols, for example ethanolamine, diethanolamine, triethanolamine or propanolamine, polyamine compounds, for example ethylenediamine, diethylenetriamine, triethylenetetramine, tetraethylenepentamine or pentaethylenehexamine, polyglycidyl ether compounds such as ethylene glycol diglycidyl ether, polyethylene glycol diglycidyl ether, glyceryl diglycidyl ether, glyceryl polyglycidyl ether, pentaerythrityl polyglycidyl ether, propylene glycol diglycidyl ether, polypropylene glycol diglycidyl ether, neopentyl glycol diglycidyl ether, hexanediol glycidyl ether, trimethylolpropane polyglycidyl ether, sorbitol polyglycidyl ether, diglycidyl phthalate, diglycidyl adipate, 1,4-phenylenebis(2-oxazoline), glycidol, polyisocyanates, preferably diisocyanates such as toluene 2,4-diisocyanate and hexamethylene diisocyanate, polyaziridine compounds such as 2,2-bishydroxymethylbutanol tris[3-(1-aziridinyl)propionate], 1,6-hexamethylenediethyleneurea and diphenylmethanebis-4,4"-N,N"-diethyleneurea, halogen epoxides, for example epichloro- and epibromohydrin and $\alpha$-methylepichlorohydrin, alkylene carbonates such as 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, 1,3-dioxolan-2-one, poly-1,3-dioxolan-2-one, polyquaternary amines such as condensation products of dimethylamines and epichlorohydrin. Preferred compounds of crosslinker class II are additionally polyoxazolines such as 1,2-ethylenebisoxazoline, crosslinkers with silane groups, such as $\gamma$-glycidoxypropyltrimethoxysilane and $\gamma$-aminopropyltrimethoxysilane, oxazolidinones such as 2-oxazolidinone, bis- and poly-2-oxazolidinones and diglycol silicates.

Preferred compounds of class III include hydroxyl- or amino-containing esters of (meth)acrylic acid, for example 2-hydroxyethyl(meth)acrylate and 2-hydroxypropyl(meth) acrylate, and also hydroxyl- or amino-containing (meth)acrylamides or mono(meth)allyl compounds of diols.

The polyvalent metal cations of crosslinker class IV derive preferably from mono- or polyvalent cations, the monovalent especially from alkali metals such as potassium, sodium, lithium, preference being given to lithium. Preferred divalent cations derive from zinc, beryllium, alkaline earth metals such as magnesium, calcium, strontium, preference being given to magnesium. Further higher-valency cations useable in accordance with the invention are cations of aluminium, iron, chromium, manganese, titanium, zirconium and other transition metals, and also double salts of such cations or mixtures of the salts mentioned. Preference is given to using aluminium salts and alums and the different hydrates thereof, for example $AlCl_3 \times 6H_2O$, $NaAl(SO_4)_2 \times 12H_2O$, $KAl(SO_4)_2 \times 12H_2O$ or $Al_2(SO_4)_3 \times 14\text{-}18H_2O$. Particular preference is given to using $Al_2(SO_4)_3$ and hydrates thereof as crosslinkers of crosslinking class IV.

The superabsorbent particles used in the process according to the invention are preferably crosslinked by crosslinkers of the following crosslinker classes, or by crosslinkers of the following combinations of crosslinker classes: I, II, III, IV, I II, I III, I IV, III III, I II IV, I III IV, II III IV, II IV or III IV. The above combinations of crosslinker classes are each a preferred embodiment of crosslinkers of a superabsorbent particle used in the process according to the invention.

Further preferred embodiments of the superabsorbent particles used in the process according to the invention are polymers which are crosslinked by any of the aforementioned crosslinkers of crosslinker classes I. Among these, preference is given to water-soluble crosslinkers. In this context, particular preference is given to N,N'-methylenebisacrylamide, polyethylene glycol di(meth)acrylates, triallylmethylammonium chloride, tetraallylammonium chloride, and allyl nonaethylene glycol acrylate prepared with 9 mol of ethylene oxide per mole of acrylic acid.

The water-soluble polymers ($\alpha 4$) present in the superabsorbent particles may be water-soluble polymers, such as partly or fully hydrolysed polyvinyl alcohol, polyvinylpyrrolidone, starch or starch derivatives, polyglycols or polyacrylic acid, preferably incorporated in polymerized form. The molecular weight of these polymers is uncritical provided that they are water-soluble. Preferred water-soluble polymers are starch or starch derivatives or polyvinyl alcohol. The water-soluble polymers, preferably synthetic water-soluble polymers such as polyvinyl alcohol, can also serve as a graft base for the monomers to be polymerized.

The assistants ($\alpha 5$) present in the polymer fines are preferably standardizers, organic or inorganic particles, for example odour binders, especially zeolites or cyclodextrins, skincare substances, surfactants or antioxidants.

The superabsorbent particles used in the process according to the invention are preferably obtainable by first preparing a water-absorbing polymer (P) in particulate form from the aforementioned monomers and crosslinkers. This polymer (P) which serves as a starting material for the superabsorbent particles is produced, for example, by bulk polymerization which is preferably effected in kneading reactors such as extruders or by belt polymerization, solution polymerization, spray polymerization, inverse emulsion polymerization or inverse suspension polymerization. Preference is given to performing the solution polymerization in water as a solvent. The solution polymerization can be effected continuously or batchwise. The prior art discloses a wide spectrum of possible variations with regard to reaction conditions, such as temperatures, type and amount of the initiators, and of the reaction solution. Typical processes are described in the following patents: U.S. Pat. No. 4,286,082, DE 27 06 135, U.S. Pat. No. 4,076,663, DE 35 03 458, DE 40 20 780, DE 42 44 548, DE 43 23 001, DE 43 33 056, DE 44 18 818. The disclosures are hereby incorporated by reference and therefore form part of the disclosure.

The initiators used to initiate the polymerization may be all initiators which form free radicals under the polymerization conditions and are typically used in the production of superabsorbents. These include thermal catalysts, redox catalysts and photoinitiators, which are activated by means of high-energy radiation. The polymerization initiators may be present dissolved or dispersed in a solution of inventive monomers. Preference is given to the use of water-soluble catalysts.

Useful thermal initiators include all compounds which decompose to free radicals under thermal action and are known to those skilled in the art. Particular preference is given to thermal polymerization initiators having a half-life of less than 10 seconds, further preferably of less than 5 seconds at less than 180° C., further preferably at less than 140° C. Peroxides, hydroperoxides, hydrogen peroxide, persulphates and azo compounds are particularly preferred polymerization initiators. In some cases, it is advantageous to use mixtures of different thermal polymerization initiators. Among these mixtures, preference is given to those of hydrogen peroxide and sodium peroxodisulphate or potassium peroxodisulphate, which can be used in any conceivable ratio. Suitable organic peroxides are preferably acetylacetone peroxide, methyl ethyl ketone peroxide, benzoyl peroxide, lauroyl peroxide, acetyl peroxide, capryl peroxide, isopropyl peroxydicarbonate, 2-ethylhexyl peroxydicarbonate, t-butyl hydroperoxide, cumene hydroperoxide, t-amyl perpivalate, t-butyl perpivalate, t-butyl perneohexanoate, t-butyl isobutyrate, t-butyl per-2-ethylhexanoate, t-butyl perisononanoate, t-butyl permaleate, t-butyl perbenzoate, t-butyl 3,5,5-trimethylhexanoate and amyl perneodecanoate. Further preferred thermal polymerization initiators are: azo compounds such as azobisisobutyronitrile, azobisdimethylvaleronitrile, 2,2'-azobis(2-amidinopropane)dihydrochloride, azobisamidinopropane dihydrochlorde, 2,2'-azobis(N,N-dimethylene)isobutyramidine dihydrochloride, 2-(carbamoylazo) isobutyronitrile and 4,4'-azobis(4-cyanovaleric acid). The compounds mentioned are used in customary amounts, preferably within a range from 0.01 to mol %, preferably from 0.1 to 2 mol %, based in each case on the amount of the monomers to be polymerized.

The redox catalysts comprise, as the oxidic component, at least one of the above-specified per compounds, and, as the reducing component, preferably ascorbic acid, glucose, sorbose, mannose, ammonium hydrogensulphite, sulphate, thiosulphate, hyposulphite or sulphide, alkali metal hydrogensulphite, sulphate, thiosulphate, hyposulphite or sulphide, metal salts such as iron(II) ions or silver ions, or sodium hydroxymethylsulphoxylate. The reducing component used in the redox catalyst is preferably ascorbic acid or sodium pyrosulphite. Based on the amount of monomers used in the polymerization, $1 \times 10^{-5}$ to 1 mol % of the reducing component of the redox catalyst and $1 \times 10^{-5}$ to 5 mol % of the oxidizing component of the redox catalyst are used. Instead of the oxidizing component of the redox catalyst, or in addition thereto, it is possible to use one or more, preferably water-soluble, azo compounds.

If the polymerization is triggered by the action of high-energy radiation, it is customary to use what are called photoinitiators as the initiator. These may be, for example, what are called α-splitters, H-abstracting systems, or else azides. Examples of such initiators are benzophenone derivatives such as Michler's ketone, phenanthrene derivatives, fluorene derivatives, anthraquinone derivatives, thioxanthone derivatives, coumarin derivatives, benzoin ethers and derivatives thereof, azo compounds such as the abovementioned free-radical initiators, substituted hexaarylbisimidazoles or acylphosphine oxides. Examples of azides are: 2-(N,N-dimethylamino)ethyl 4-azidocinnamate, 2-(N,N-dimethylamino)ethyl 4-azidonaphthyl ketone, 2-(N,N-dimethylamino)ethyl 4-azidobenzoate, 5-azido-1-naphthyl 2'-(N,N-dimethylamino)ethyl sulphone, N-(4-sulphonylazidophenyl) maleimide, N-acetyl-4-sulphonylazidoaniline, 4-sulphonylazidoaniline, 4-azidoaniline, 4-azidophenacyl bromide, p-azidobenzoic acid, 2,6-bis(p-azidobenzylidene) cyclohexanone and 2,6-bis(p-azidobenzylidene)-4-methylcyclohexanone. The photoinitiators are, if they are used, employed typically in amounts of 0.01 to 5% by weight, based on the monomers to be polymerized.

Preference is given in accordance with the invention to using a redox system consisting of hydrogen peroxide, sodium peroxodisulphate and ascorbic acid. In general, the polymerization is initiated with the initiators within a temperature range from 0° C. to 90° C.

The polymerization reaction can be triggered by one initiator or by a plurality of interacting initiators. In addition, the polymerization can be performed in such a way that one or more redox initiators are first added. Later in the polymerization, thermal initiators or photoinatators are then applied additionally, and the polymerization reaction in the case of photoinitiators is then initiated by the action of high-energy radiation. The reverse sequence, i.e. the initial initiation of the reaction by means of high-energy radiation and photoinitiators or thermal initiators and initiation of the polymerization by means of one or more redox initiators later in the polymerization, is also conceivable.

In order to convert the polymers (P) thus obtained to a particulate form, they can first, after they have been removed from the reaction mixture, be dried at a temperature within a range from 20 to 300° C., preferably within a range from 50 to 250° C. and more preferably within a range from 100 to 200° C., down to a water content of less than 40% by weight, preferably of less than 20% by weight and further preferably of less than 10% by weight, based in each case on the total weight of the polymer (P). The drying is effected preferably in ovens or driers known to those skilled in the art, for example in belt driers, staged driers, rotary tube ovens, fluidized bed driers, pan driers, paddle driers or infrared driers.

According to the present invention, the comminution is preferably effected by dry grinding, preferably by dry grinding in a hammer mill, a pinned disc mill, a ball mill or a roll mill.

In a preferred embodiment of the process according to the invention, the superabsorbent particles used are particles which have an inner region and a surface region bordering the inner region, the surface region having a different chemical composition from the inner region or differing from the inner region in a physical property. Physical properties in which the inner region differs from the surface region are, for example, the charge density or the degree of crosslinking.

These superabsorbent particles which have an inner region and a surface region bordering the inner region are preferably obtainable by postcrosslinking reactive groups close to the surface of the superabsorbent particles before or after they have been removed from the remaining particles of the particulate polymer (P). This postcrosslinking can be effected thermally, photochemically or chemically.

Preferred postcrosslinkers are the compounds of crosslinker classes II and IV mentioned in connection with the crosslinkers ($\alpha 3$).

Among these compounds, particularly preferred postcrosslinkers are diethylene glycol, triethylene glycol, polyethylene glycol, glycerol, polyglycerol, propylene glycol, diethanolamine, triethanolamine, polyoxypropylene, oxyethylene-oxypropylene block copolymers, sorbitan fatty acid esters, polyoxyethylenesorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, 1,3-dioxolan-2-one, poly-1,3-dioxolan-2-one. Particular preference is given to using ethylene carbonate as the postcrosslinker.

Preferred embodiments of the superabsorbent particles are those which are postcrosslinked by crosslinkers of the following crosslinker classes or by crosslinkers of the following combinations of crosslinker classes: II, IV and II IV.

The crosslinker is preferably used in an amount within a range from 0.01 to 30% by weight, more preferably in an amount within a range from 0.1 to 20% by weight and further preferably in an amount within a range from 0.3 to 5% by weight, based in each case on the weight of the superabsorbent polymers in the postcrosslinking.

It is likewise preferred that the postcrosslinking is effected by contacting a fluid $F_1$ comprising a solvent, preferably water, with water-miscible organic solvents, for example methanol or ethanol or mixtures of at least two thereof, and the postcrosslinker with the outer region of the polymer particles at a temperature within a range from 30 to 300° C., more preferably within a range from 100 to 200° C. The contacting is preferably effected by spraying the fluid $F_1$ onto the polymer particles and then mixing the polymer particles contacted with the fluid $F_1$. The postcrosslinker is present in the fluid $F_1$ preferably in an amount within a range from 0.01 to 20% by weight, more preferably in an amount within a range from 0.1 to 10% by weight, based on the total weight of the fluid $F_1$. It is additionally preferred that the fluid $F_1$ is contacted with the polymer particles in an amount within a range from 0.01 to 50% by weight, more preferably in an amount within a range from 0.1 to 30% by weight, based in each case on the weight of the polymer particles.

The fluid used in process step (vii) in the processes according to the invention preferably comprises a solvent and the crosslinkable, uncrosslinked polymer. The solvents used are preferably water or polar, water-miscible solvents such as acetone, methanol, ethanol, 2-propanol or mixtures of at least two thereof. The uncrosslinked polymer may be dissolved or dispersed in the solvent.

In a preferred embodiment of the process according to the invention, the fluid includes from 18 to 70% by weight and more preferably from 19 to 55% by weight, based in each case on the fluid, of the crosslinkable, uncrosslinked polymer.

The crosslinkable, uncrosslinked polymer is based preferably on ($\beta 1$) 20 to 100% by weight, preferably 50 to 98.99% by weight and more preferably 90 to 98.95% by weight of polymerized, ethylenically unsaturated monomers containing acid groups or salts thereof, ($\beta 2$) 0 to 70% by weight, preferably 1 to 60% by weight and more preferably 1 to 40% by weight of polymerized, ethylenically unsaturated monomers copolymerizable with ($\alpha 1$), and ($\beta 3$) 0 to 10% by weight, preferably 0.01 to 7% by weight and more preferably 0.05 to 5% by weight of the monomer which can react with polymerized monomers bearing acid groups, preferably with polymerized monomers containing acid groups in the surface region of the superabsorbent particles or with other polymerized monomers (M) containing acid groups in the crosslinkable, uncrosslinked polymer, in a condensation reaction, in an addition reaction or in a ring-opening reaction, preferably with an energy input, where the sum of components ($\beta 1$) to ($\beta 3$) is 100% by weight.

Useful condensation reactions preferably include the formation of ester, amide, imide or urethane bonds, preference being given to the formation of ester bonds. These ester bonds are preferably formed by the reaction of an OH group of the crosslinkable, uncrosslinked polymer with an acid group of the superabsorbent particle or with an acid group of the crosslinkable, uncrosslinked polymer.

The monomers ($\beta 1$) containing acid groups are preferably neutralized to an extent of at least 10 mol %, more preferably to an extent of at least 20 mol %, further preferably to an extent of at least 40 mol % and even further preferably in the range from 45 to 80 mol %. The monomers can be neutralized before, during or only after the preparation of the crosslinkable, uncrosslinked polymer. The neutralization is preferably effected with the same bases which have already been mentioned in connection with the neutralization of the monomers ($\alpha 1$) bearing acid groups. In addition to the bases mentioned there, the uncrosslinked polymers are preferably also neutralized using bases which contain ammonium, calcium or magnesium as cations. Bases preferred in this context are ammonium carbonate, ammonia, calcium carbonate, calcium hydroxide, magnesium hydroxide and magnesium carbonate.

The monomers ($\beta 1$) and ($\beta 2$) used are preferably those monomers which are also used as preferred monomers ($\alpha 1$) and ($\alpha 2$) respectively.

In principle, useful monomers (M) or ($\beta 3$) are all monomers known to be suitable to the person skilled in the art, especially those of crosslinker class III. Preferred monomers ($\beta 3$) are the reaction products of saturated aliphatic, cycloaliphatic, aromatic alcohols, amines or thiols with ethylenically unsaturated carboxylic acids, reactive carboxylic acid derivatives or allyl halides. Examples in this context include: (meth)allyl alcohol, (meth)allylamine, hydroxyl- or amino-containing esters of (meth)acrylic acid, such as hydroxyalkyl acrylates, especially hydroxymethyl(meth)acrylate, 2-hydroxyethyl(meth)acrylate or 2-hydroxypropyl (meth)acrylate, aminoalkyl(meth)acrylates, especially aminomethyl(meth)acrylate, 2-aminoethyl(meth)acrylate or 2-aminopropyl(meth)acrylate, mono(meth)allyl compounds of polyols, preferably of diols, for example polyethylene glycols or polypropylene glycols, and glycidylalkyl(meth)acrylates such as glycidyl(meth)acrylate.

Particularly preferred crosslinkable, uncrosslinked polymers which are used in the processes according to the invention are those polymers based on 1 to 80% by weight, more preferably on 1 to 60% by weight and further preferably on 1 to 20% by weight of (meth)acrylamide and 20 to 99% by weight, more preferably on 40 to 99% by weight and further preferably on 80 to 99% by weight, based in each case on the total weight of the uncrosslinked polymer, on (meth)acrylic acid, the (meth)acrylic acid being preferably partly neutralized.

It is additionally preferred that the fluid used in the process according to the invention, in addition to the solvent and the crosslinkable, uncrosslinked polymer, comprises a further external crosslinker. This is especially true when the crosslinkable, uncrosslinked polymers do not include any monomers (M) or (β3). Preferred further external crosslinkers are those of crosslinker classes II and IV which have already been mentioned in connection with the crosslinkers (α3). Particularly preferred further crosslinkers are those which have been mentioned as particularly preferred crosslinkers of classes II and IV in connection with the monomers (α3). It is further preferred in this context that the fluid comprises the further external crosslinker in an amount within a range from 0.01 to 30% by weight, preferably within a range from 0.1 to 15% by weight and more preferably within a range from 0.2 to 7% by weight, based on the weight of the uncrosslinked polymer.

Preferred additives are substances which reduce the brittleness of the superabsorbent particles produced by the process according to the invention, for instance polyethylene glycol, polypropylene glycol, mixed polyalkoxylates, polyalkoxylates based on polyols such as glycerol, trimethylolpropane or butanediol, surfactants with an HLB of more than 10, such as alkyl polyglucosides or ethoxylated sugar esters, for example polysorbates under the Tween trade name from ICI. Some of these additives also act simultaneously as further crosslinkers, for example polyethylene glycol, polypropylene glycol, trimethylolpropane or butanediol.

Further preferred additives are agents which reduce the hardness of the superabsorbent particles produced by the process according to the invention, for example cationic surfactants such as alkyltrimethylammonium chloride, dialkyldimethylammonium chloride, dimethylstearylammonium chloride, alkylbenzyldimethylammonium chloride, or the corresponding methylsulphates, quaternary tall oil fatty acid imidazolinium methosulphates. These additives are preferably used in amounts within a range from 0 to 5% by weight, more preferably within a range from 0.5 to 4% by weight, based on the weight of the uncrosslinked polymer. The additives can be added either before or after the polymerization. They bind the polycarboxylates by anion-cation interaction and thus bring about the softening effect. They simultaneously bring about an improvement in the absorption capacity for aqueous liquids. Another advantage of the substances is the biocidal action thereof, which prevents unwanted degradation of the swelling agents. This property is particularly important for some applications.

Preferred additives are additionally release agents, for instance inorganic or organic pulverulent release agents. These release agents are preferably used in amounts within a range from 0 to 2% by weight, more preferably within a range from 0.1 to 1.5% by weight, based on the weight of the crosslinked polymer. Preferred release agents are wood flour, pulp fibres, powdered bark, cellulose powder, mineral fillers such as perlite, synthetic fillers such as nylon powder, rayon powder, diatomaceous earth, bentonite, kaolin, zeolites, talc, loam, ash, carbon dust, magnesium silicates, fertilizers or mixtures of the substances. Finely divided fumed silica, as sold under the Aerosil trade name by Evonik Degussa, is preferred.

In a preferred embodiment of the process according to the invention, the superabsorbent particles are contacted with the fluid comprising the uncrosslinked polymer in the presence of an effect substance based on a polysugar or a compound containing silicon-oxygen or a mixture of at least two thereof. The effect substance may be present in the fluid or else may be mixed with the superabsorbent particles before the contacting of the superabsorbent particles with the fluid. It is also possible that the effect substance is dissolved or dispersed in a further fluid F' and is contacted with the superabsorbent particles in the form of this solution or dispersion together with the fluid. The fluid F' comprises, in addition to the effect substance, preferably a liquid, particularly preferred liquids being water and organic solvents, for example methanol or ethanol, or else mixtures of at least two thereof, particular preference being given to water as the liquid.

Useful polysugars in accordance with the invention include all starches familiar to the person skilled in the art and derivatives thereof, and also celluloses and derivatives thereof, and cyclodextrins, the cyclodextrins used being preferably α-cyclodextrin, β-cyclodextrin, γ-cyclodextrin or mixtures of these cyclodextrins.

Preferred compounds containing silicon-oxygen are zeolites. The zeolites used may be all synthetic or natural zeolites known to those skilled in the art. Preferred natural zeolites are zeolites from the natrolite group, the harmotome group, the mordenite group, the chabazite group, the faujasite group (sodalite group) or the analcite group. Examples of natural zeolites are analcime, leucite, pollucite, wairakite, bellbergite, bikitaite, boggsite, brewsterite, chabazite, willhendersonite, cowlesite, dachiardite, edingtonite, epistilbite, erionite, faujasite, ferrierite, amicite, garronite, gismondine, gobbinsite, gmelinite, gonnardite, goosecreekite, harmotome, phillipsite, wellsite, clinoptilolite, heulandite, laumontite, levyne, mazzite, merlinoite, montesommaite, mordenite, mesolite, natrolite, scolecite, offretite, paranatrolite, paulingite, perlialite, barrerite, stilbite, stellerite, thomsonite, tschernichite or yugawaralite. Preferred synthetic zeolites are zeolite A, zeolite X, zeolite Y, zeolite P, or the product ABSCENTS.

The cations present in the zeolites used in the process according to the invention are preferably alkali metal cations such as $Li^+$, $Na^+$, $K^+$, $Rb^+$, $Cs^+$ or $Fr^+$ and/or alkaline earth metal cations such as $Mg^{2+}$, $Ca^{2+}$, $Sr^{2+}$ or $Ba^{2+}$.

The zeolites used may be zeolites of what is called the "intermediate" type, in which the $SiO_2/AlO_2$ ratio is less than 10; the $SiO_2/AlO_2$ ratio of these zeolites is more preferably within a range from 2 to 10. In addition to these "intermediate" zeolites, it is also possible to use zeolites of the "high" type, which include, for example, the known "molecular sieve" zeolites of the ZSM type, and beta-zeolite. These "high" zeolites are preferably characterized by an $SiO_2/AlO_2$ ratio of at least 35, more preferably by an $SiO_2/AlO_2$ ratio within a range from 200 to 500.

The zeolites are preferably used in the form of particles with a mean particle size within a range from 1 to 500 μm, more preferably within a range from 2 to 200 μm and further preferably within a range from 5 to 100 μm.

The effect substances are used in the processes according to the invention preferably in an amount within a range from 0.1 to 50% by weight, more preferably within a range from 1 to 40% by weight and further preferably in an amount within a range from 5 to 30% by weight, based in each case on the weight of the superabsorbent particles.

Preferred microbe-inhibiting substances are in principle all substances active against Gram-positive bacteria, for example 4-hydroxybenzoic acid and salts and esters thereof, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbonilide (TTC), antibacterial fragrances, thymol, thyme oil, eugenol, clove oil, menthol, mint oil, farnesol, phenoxyethanol, glyceryl monocaprinate, glyceryl monocaprylate, glyceryl monolaurate (GML), diglyceryl monocaprinate (DMC), N-alkylsalicylamides, for example N-octylsalicylamide or N-decylsalicylamide.

Suitable enzyme inhibitors are, for example, esterase inhibitors. These are preferably trialkyl citrates such as trimethyl citrate, tripropyl citrate, triisopropyl citrate, tributyl citrate and especially triethyl citrate (Hydagen™ CAT, Cognis GmbH, Dusseldorf, Germany). The substances inhibit enzyme activity and as a result reduce odour formation. Further substances useful as esterase inhibitors are sterol sulphates or phosphates, for example lanosterol sulphate or phosphate, cholesterol sulphate or phosphate, campesterol sulphate or phosphate, stigmasterol sulphate or phosphate and sitosterol sulphate or phosphate, dicarboxylic acids and esters thereof, for example glutaric acid, monoethyl glutarate, diethyl glutarate, adipic acid, monoethyl adipate, diethyl adipate, malonic acid and diethyl malonate, hydroxycarboxylic acids and esters thereof, for example citric acid, malic acid, tartaric acid or diethyl tartrate, and zinc glycinate. Suitable odour absorbers are substances which can adsorb and substantially retain odour-forming substances. They lower the partial pressure of the individual components and thus also the rate of spread thereof. It is important that perfumes must remain unimpaired. Odour absorbers have no effect against bacteria. They contain, for example, as the main constituent, a complex zinc salt of ricinoleic acid or specific, substantially odour-neutral fragrances known as "fixatives", for example extracts of labdanum or styrax or particular abietic acid derivatives. The function of odour maskers is fulfilled by odorants or perfume oils which, in addition to their function as odour maskers, impart their particular fragrance notes to the deodorants. Examples of perfume oils include mixtures of natural and synthetic odorants. Natural odorants are extracts of flowers, stems and leaves, fruits, fruit skins, roots, woods, herbs and grasses, needles and twigs, and also resins and balsams. Additionally useful are animal raw materials, for example civet and castoreum. Typical synthetic odorant compounds are products of the ester, ether, aldehyde, ketone, alcohol and hydrocarbon type. Odorant compounds of the ester type are, for example, benzyl acetate, p-tert-butylcyclohexyl acetate, linalyl acetate, phenylethyl acetate, linalyl benzoate, benzyl formate, allylcyclohexyl propionate, styrallyl propionate and benzyl salicylate. The ethers include, for example, benzyl ethyl ether; the aldehydes include, for example, the linear alkanals having 8 to 18 carbon atoms, citral, citronellal, citronellyloxyacetaldehyde, cyclamen aldehyde, hydroxycitronellal, lilial and bourgeonal; the ketones include, for example, the ionones and methyl cedryl ketone; the alcohols include anethole, citronellol, eugenol, isoeugenol, geraniol, linalool, phenylethyl alcohol and terpineol; the hydrocarbons include principally the terpenes and balsams. Preference is given, however, to using mixtures of different odorants which together produce a pleasing fragrance note. Suitable perfume oils are also essential oils of relatively low volatility which are usually used as aroma components, for example sage oil, camomile oil, clove oil, melissa oil, mint oil, cinnamon leaf oil, lime blossom oil, juniperberry oil, vetiver oil, olibanum oil, galbanum oil, labdanum oil and lavender oil. Preference is given to using bergamot oil, dihydromyrcenol, lilial, lyral, citronellol, phenylethyl alcohol, alpha-hexylcinnamaldehyde, gerani oil, benzylacetone, cyclamen aldehyde, linalool, Boisambrene Forte, ambroxan, indole, Hedione, Sandelice, lemon oil, mandarin oil, orange oil, allyl amyl glycolate, cyclovertal, lavender oil, clary sage oil, beta-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, Romilat, Irotyl and Floramat, alone or in mixtures.

Antiperspirants reduce the formation of perspiration by influencing the activity of the eccrine sweat glands, and thus counteract underarm wetness and body odour. Suitable astringent active antitranspirant ingredients are in particular salts of aluminium, zirconium or zinc. Such suitable antihydrotically active ingredients are, for example, aluminium chloride, aluminium chlorohydrate, aluminium dichlorohydrate, aluminium sesquichlorohydrate and the complexes thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and the complexes thereof, for example with amino acids such as glycine.

Suitable apparatuses for mixing or spraying are all of those which allow homogeneous distribution of the fluid on or with the superabsorbent particles. Examples are Lödige mixers (manufactured by Gebrüder Lödige Maschinenbau GmbH), Gericke multi-flux mixers (manufactured by Gericke GmbH), DRAIS mixers (manufactured by DRAIS GmbH Spezialmaschinenfabrik Mannheim), Hosokawa mixers (Hosokawa Mokron Co., Ltd.), Ruberg mixers (manufactured by Gebr. Ruberg GmbH & Co. KG Nieheim), Hüttlin coaters (manufactured by BWI Hüttlin GmbH Steinen), fluidized bed driers or spray granulators from AMMAG (manufactured by AMMAG Gunskirchen, Austria) or Heinen (manufactured by A. Heinen AG Anlagenbau Varel), Patterson-Kelly mixers, NARA paddle mixers, screw mixers, pan mixers, fluidized bed driers, Schugi mixers or PROCESSALL.

For contacting in a fluidized bed, it is possible to employ all fluidized bed processes which are known to those skilled in the art and appear to be suitable. For example, it is possible to use a fluidized bed coater.

A further contribution to the achievement of the objects described at the outset is made by a composite including the inventive superabsorbents or the superabsorbents obtainable by the process according to the invention and a substrate. It is preferable that the inventive superabsorbents and the substrate are bonded in a fixed manner to one another. Preferred substrates are films of polymers, for example of polyethylene, polypropylene or polyamide, metals, nonwovens, fluff, tissues, fabrics, natural or synthetic fibres, or other foams. It is additionally preferred in accordance with the invention that the composite comprises at least one region which includes the inventive superabsorbent in an amount in the range from about 15 to 100% by weight, preferably about 30 to 100% by weight, more preferably of about 50 to 99.99% by weight, further preferably from about 60 to 99.99% by weight and even further preferably from about 70 to 99% by weight, based in each case on the total weight of the region of the composite in question, this region preferably having a size of at least 0.01 $cm^3$, preferably at least 0.1 $cm^3$ and most preferably at least 0.5 $cm^3$.

A particularly preferred embodiment of the inventive composite involves a flat composite as described in WO 02/056812 A1 as an "absorbent material". The disclosure-content of WO 02/056812 A1, especially with regard to the exact structure of the composite, the basis weight of the constituents thereof and the thickness thereof, is hereby incorporated by reference and forms part of the disclosure of the present invention.

A further contribution to the achievement of at least one of the objects stated at the outset is made by a process for producing a composite, wherein the inventive water-absorbing polymers or the superabsorbents obtainable by the process according to the invention and a substrate and optionally an additive are contacted with one another. The substrates used are preferably those substrates which have already been mentioned above in connection with the inventive composite.

A contribution to the achievement of at least one of the objects stated at the outset is also made by a composite obtainable by the process described above, this composite preferably having the same properties as the above-described inventive composite.

A further contribution to the achievement of at least one of the objects stated at the outset is made by chemical products including the inventive superabsorbents or an inventive composite. Preferred chemical products are especially foams, mouldings, fibres, foils, films, cables, sealing materials, liquid-absorbing hygiene articles, especially nappies and sanitary towels, carriers for plant growth or fungal growth regulators or plant protection active ingredients, additives for building materials, packaging materials or soil additives.

The use of the inventive superabsorbents or of the inventive composite in chemical products, preferably in the aforementioned chemical products, especially in hygiene articles such as nappies or sanitary towels, and the use of the superabsorbent particles as carriers for plant growth or fungal growth regulators or plant protection active ingredients makes a contribution to the achievement of at least one of the objects stated at the outset. In the case of use as a carrier for plant growth or fungal growth regulators or plant protection active ingredients, it is preferred that the plant growth or fungal growth regulators or plant protection active ingredients can be released over a period controlled by the carrier.

Test Methods

Unless stated otherwise hereinafter, the measurements conducted herein are performed according to ERT methods. "ERT" stands for EDANA Recommended Test and "EDANA" for European Disposables and Nonwovens Association.

Absorption Against a Pressure of 0.3 or 0.7 Psi (AAP)

The absorption under pressure was determined as AAP (Absorption at Pressure) to ERT 442-2-02 on the entire particle fraction. The liquid absorption capacity against an external pressure (Absorption Against Pressure, AAP) was determined according to EDANA method No. 442.1-99. 0.90 g of the test substance (sieved between 150 and 850 μm) were weighed into a test cylinder with internal diameter 60.0 mm and a sieve base (400 mesh) (concentration: 0.032 g/cm$^2$) and distributed homogeneously. A cylindrical weight (21 g/cm$^2$=0.3 psi or 50 g/cm$^2$=0.7 psi) with an external diameter of 59.2 mm is placed onto the test substance. Filter plates covered with a filter paper are placed into a plastic dish. The plastic dish is filled with 0.9% NaCl solution until the liquid level concludes with the upper edge of the filter plates. Subsequently, the prepared measurement units are placed onto the filter plates. After a swell time of 60 minutes, the measurement units are removed and the weight is removed. The amount of liquid absorbed is determined gravimetrically and converted to 1 gram of test substance.

Determination of the Free Swell Rate (FSR)

The absorption rate was determined via the measurement of the Free Swell Rate (FSR) by the test method described in EP-A-0 443 627 on page 12.

Centrifuge Retention Capacity (CRC)

The centrifuge retention capacity is determined by EDANA (European Disposables and Nonwovens Association) recommended test method No. 441.2-02 "Centrifuge retention capacity".

Specific Surface Area, BET Measurement

The specific surface area was determined using a Gemini VII 2390 p with an evacuation rate of 1000.00 mmHg/min. The adsorbent used was nitrogen. The equilibration time was in each case 5 sec and the saturation pressure was 756.144 mmHg.

EXAMPLES

A monomer solution consisting of 300 g of acrylic acid which had been neutralized to an extent of 70 mol % with sodium hydroxide solution (233.14 g of 50% NaOH), 442.81 g of water, 0.622 g of polyethylene glycol-300 diacrylate, 1.043 g of monoallyl polyethylene glycol-450 monoacrylic ester is freed of dissolved oxygen by purging with nitrogen and cooled to the start temperature of approx. 4° C. Once the start temperature had been attained, an initiator solution was added (0.3 g of sodium peroxodisulphate in 10 g of water, 0.07 g of 35% hydrogen peroxide in 10 g of water and 0.015 g of ascorbic acid in 2 g of water). An exothermic polymerization reaction takes place. The adiabatic end temperature was approx. 105° C. The hydrogel formed was comminuted with a laboratory meat grinder. The subsequent further procedure was as described in a) to c):

Reference Sample

Without further additional treatment, the reference sample which had been coarsely comminuted with a meat grinder was dried at 150° C. in a laboratory forced air drying cabinet for two hours.

a) Overall, 2 kg of a gel coarsely comminuted with a meat grinder were divided between two large photographic trays. Beforehand, 5-15 kg of dry ice pellets had been ground to a fine powder in a Retsch centrifugal mill at setting 2. This was added uniformly to the still-warm gel. After approx. 5 minutes, the gel which had already solidified slightly was turned over and covered again with dry ice. This operation was repeated until all of the gel had solidified (2 to 4 repetitions). Then the solidified gel was coarsely manually comminuted, such that the fragments fitted into the Retsch centrifugal mill. The mill had been cooled beforehand (for example with dry ice). The frozen gel was also additionally mixed with 1-3 kg of dry ice pellets. This brings about compensation for the evolution of heat during the grinding operation. Grinding was effected at setting 1 with a 5 mm perforated ring in the Retsch centrifugal mill. After the grinding, quite fine but still frozen superabsorbent particles were present, which were distributed homogeneously onto drying grids and then dried in a laboratory forced-air drying cabinet at 150° C. for 2 hours.

b) 1 kg of a gel coarsely comminuted with a meat grinder was distributed homogeneously onto drying grids and dried in a laboratory forced-air drying cabinet at 150° C. for 2 hours. The dried superabsorbent was then mixed with approx. 2-5 kg of pulverized dry ice. After approx. 15-25 minutes, the frozen superabsorbent particles were comminuted with a centrifugal mill which had been cooled beforehand. In order to reduce heating of the mill during the comminution operation, the mill was cooled in the meantime with 250-500 g of dry ice pellets. Comminution was effected at setting 1 with a 5 mm perforated ring. The mixture was then distributed between two metal dishes and introduced into the laboratory forced-air drying cabinet at 50° C. for approx. 2 hours.

c) In the case of this amendment in the procedure, only the centrifugal mill was cooled, i.e. the gel coarsely comminuted with a meat grinder is distributed homogeneously on drying grids and dried in a laboratory forced-air drying cabinet at 150° C. for 2 hours. The dried superabsorbent is mixed with dry ice pellets and immediately thereafter introduced into the centrifugal mill which had been cooled beforehand and ground (setting 1, 5 mm perforated ring). This was followed by further drying of the slightly swollen superabsorbent by drying at 50° C. for 2 hours in a laboratory forced-air drying cabinet.

All samples have a particle size distribution in the range from 150 to 850 μm, with 80% of the particle size distribution present in the range from 300 to 600 μm.

| Process | CRC (g/g) | FSR (g/g sec) |
|---|---|---|
| A | 34.3 | 0.51 |
| B | 33.4 | 0.19 |
| C | 33.5 | 0.25 |
| Reference | 33.3 | 0.25 |

An increase in the Free Swell Rate (FSR) was found for superabsorbent particles according to process a). Reference and superabsorbents b) and c) do not have increased FSR values.

Results after Postcrosslinking on Laboratory Scale:

All samples had a particle size distribution in the range from 150 to 850 μm, with 80% of the particle size distribution present in the range from 300 to 600 μm. The postcrosslinking was effected by means of a mixture of ethylene carbonate, aluminium lactate and/or aluminium sulphate in water at elevated temperatures, as shown in the table below.

The reference sample and the samples described in a) to c) were postcrosslinked.

| Process | Temp/time [° C./min] | CRC (g/g) | AAP (g/g) | FSR (g/g sec) |
|---|---|---|---|---|
| Reference | 180/30 | 27.0 | 24.9 | 0.19 |
| A | 180/30 | 27.3 | 24.6 | 0.57 |
| B | 180/30 | 26.4 | 23.1 | 0.25 |
| C | 180/30 | 26.9 | 24.5 | 0.22 |
| Reference | 170/90 | 26.1 | 24.4 | 0.21 |
| A | 170/90 | 26.4 | 23.9 | 0.57 |
| B | 170/90 | 27.5 | 24.8 | 0.23 |
| C | 170/90 | 27 | 24.6 | 0.26 |

Only the samples which had been produced according to a) have an elevated FSR.

Performance of Cryogenic Grinding with Liquid Nitrogen as a Coolant

The gel coarsely comminuted with a meat grinder was first cooled slightly under ambient air. The centrifugal mill was cooled by means of dry ice beforehand. Small amounts of gel which were still lukewarm were introduced into a Dewar vessel filled with liquid nitrogen. These remained in the Dewar vessel until the increased gas formation in the Dewar abated. The gel fell apart into smaller pieces. These pieces were then removed from the Dewar vessel by means of a sieve and ground with the cooled centrifugal mill (setting 1, 5 mm perforated ring). The comminuted frozen material was removed from the mill and then distributed homogeneously onto drying grids. This was followed by drying in a laboratory forced-air drying cabinet at 150° C. over 2 h.

Results:

All samples have a particle size distribution in the range from 150 to 850 μm, with 80% of the particle size distribution present in the range from 300 to 600 μm.

| Method | Temp/time [min/° C.] | CRC (g/g) | AAP (g/g) | FSR (g/g sec) |
|---|---|---|---|---|
| Reference | 180/30 | 33.7 | — | 0.27 |
| Liq. nitrogen | 180/30 | 30.4 | — | 0.52 |
| Reference | 180/30 | 28.8 | 25.5 | 0.21 |
| Liq. nitrogen | 170/90 | 27.0 | 24.1 | 0.55 |
| Reference | 170/90 | 27.8 | 24.3 | 0.20 |
| Liq. nitrogen | 170/90 | 27.2 | 24.6 | 0.56 |

Compared to the reference sample, the cryogenically ground sample was one for which liquid nitrogen was used as the coolant and led to an increase in the FSR.

In a further test series, different mixing ratios of the cryogenically treated, water-absorbing material with untreated water-absorbing material were conducted. In addition, tests were conducted with postcrosslinked material, either cryogenically ground in accordance with the invention or untreated. The postcrosslinking was effected by means of a mixture of ethylene carbonate, aluminium lactate and/or aluminium sulphate in water at relatively high temperatures, as shown in the table below.

In the first series of tests, water-absorbing material without cryogenic treatment and water-absorbing material with cryogenic treatment were analysed for CRC, AAP and FSR values. It was found here that the cryogenic product treated in accordance with the invention had higher CRC and FSR values.

After a postcrosslinking step as described above, the measurements on the samples were repeated. It was found here that only in the postcrosslinking step can an AAP be measured. The CRC and FSR values were reduced compared to the non-postcrosslinked materials.

| Sample | Surface crosslinking | Temp/time ° C./min | CRC (g/g) | AAP (g/g) | FSR (g/g sec) |
|---|---|---|---|---|---|
| Untreated sample | − | — | 33.7 | — | 0.33 |
| Cryogenic sample | − | — | 34.5 | — | 0.60 |
| Untreated sample | + | 170/90 | 29.7 | 26.4 | 0.23 |
| Cryogenic sample | + | 170/90 | 28.5 | 25.1 | 0.45 |

In the second series, mixtures of water-absorbing material without cryogenic treatment and water-absorbing material with cryogenic treatment were analysed for CRC, AAP and FSR values.

| Mixing ratio % Untreated | Mixing ratio % Cryogenic | Characteristics | |
|---|---|---|---|
| | | CRC (g/g) | FSR (g/g sec) |
| 100 | 0 | 37.7 | 0.33 |
| 0 | 100 | 34.5 | 0.60 |
| 50 | 50 | 34.6 | 0.33 |
| 75 | 25 | 33.8 | 0.28 |
| 90 | 10 | 33.9 | 0.28 |

Determination of the BET Surface Area of Cryogenically Ground Superabsorbent Material The specific surface area was determined using a Gemini VII 2390 p with an evacuation rate of 1000.00 mmHg/min. The adsorbent used was nitrogen. The equilibration time was in each case 5 sec and the saturation pressure: 756.144 mmHg. The sample weight of the cryogenically ground sample was 4.3835 g and the weight of the sample treated not in accordance with the invention 5.3201 g. The specific surface area of the cryogenically ground product is increased compared to the reference sample which has not been ground cryogenically, as can be seen in the table below.

| Sample | FSR [g/g s] | CRC [g/g] | BET surface area [m$^2$/g] |
|---|---|---|---|
| Sample, cryogenically ground | 0.45 | 28.5 | 1.49 |
| Sample, not cryogenically ground | 0.23 | 29.7 | 0.85 |

The invention claimed is:

1. A process for producing a water-absorbing polymer comprising:
   (i) mixing
   ($\alpha$1) 0.1 to 99.99% by weight ethylenically unsaturated monomers containing acid groups or salts thereof, or ethylenically unsaturated monomers including a protonated or quaternized nitrogen, or mixtures thereof,
   ($\alpha$2) 0 to 70% by weight ethylenically unsaturated monomers copolymerizable with ($\alpha$1),
   ($\alpha$3) 0.001 to 10% by weight of one or more crosslinkers,
   ($\alpha$4) 0 to 30% by weight of water-soluble polymers, and
   ($\alpha$5) 0 to 20% by weight of one or more assistants, where the sum of the weights ($\alpha$1) to ($\alpha$5) is 100% by weight;
   (ii) free-radical polymerization with crosslinking to form a water-insoluble aqueous untreated hydrogel polymer;
   (iii) coarse comminution of the untreated hydrogel polymer to give pieces having a diameter in the range from 0.1 mm to 5.0 cm;
   (iv) cooling the coarsely comminuted untreated hydrogel polymer and grinding the cooled untreated hydrogen polymer;
   (v) drying the comminuted untreated hydrogel polymer after grinding at a temperature in the range from 85° C. to 260° C., and sieving the dried pieces in the range from 150 μm to 850 μm;
   (vi) postcrosslinking the hydrogel polymer and
   (vii) drying and finishing the water-absorbing polymer, wherein the cooling is carried out at a temperature of −30° C. to −200° C.

2. The process according to claim 1, wherein after step (ii), the hydrogel polymer still at reaction temperature is comminuted in a first step and then cooled in a cooling region to −30° C. to −200° C. and comminuted further.

3. The process according to claim 2, wherein the comminuted untreated hydrogel polymer is cooled in the cooling region over a period of 30 sec to 3600 sec before it is processed further.

4. The process according to claim 2, wherein the comminuted untreated hydrogel polymer is cooled using coolants that are inert solid or liquid refrigerants from the group of CO, carbon dioxide, inert hydrocarbons, halogenated hydrocarbons, nitrogen, helium, argon, or mixtures thereof.

5. The process according to claim 2, wherein the cooling region has at least one cooling zone.

6. The process according to claim 2, wherein the cooling region has at least two cooling zones.

7. The process according to claim 2, wherein the cooling region has a temperature gradient.

8. The process according to claim 2, wherein the cooling region has, in the end region, a cooled apparatus for comminution of the comminuted untreated hydrogel polymer.

9. The process according to claim 1, wherein the water-absorbing polymer has an FSR of at least 0.3.

10. The process according to claim 1, wherein the water-absorbing polymer is mixed with standard superabsorbents in step (ii) and/or (iii) or steps (v) to (vii).

11. The process according to claim 1, wherein the water-absorbing polymer is mixed with standard superabsorbents in steps (v) to (vii).

12. The process according to claim 1, wherein the water-absorbing polymer and an assistant are contacted with one another.

* * * * *